US009538864B2

(12) United States Patent
Williams

(10) Patent No.: US 9,538,864 B2
(45) Date of Patent: Jan. 10, 2017

(54) PHLEBOTOMIST'S UTILITY RACK WITH ATTACHMENT FEATURES

(71) Applicant: Stephanie Williams, Las Vegas, NV (US)

(72) Inventor: Stephanie Williams, Las Vegas, NV (US)

( * ) Notice: Subject to any disclaimer, the term of this patent is extended or adjusted under 35 U.S.C. 154(b) by 0 days.

(21) Appl. No.: 13/555,061

(22) Filed: Oct. 9, 2012

(65) Prior Publication Data

US 2013/0112636 A1    May 9, 2013

(51) Int. Cl.
*A47F 7/00* (2006.01)
*A47G 29/087* (2006.01)
*A61G 7/05* (2006.01)
*A61G 12/00* (2006.01)
*A61J 1/16* (2006.01)

(52) U.S. Cl.
CPC ............ *A47F 7/00* (2013.01); *A61B 50/20* (2016.02); *A61B 50/22* (2016.02); *A61G 7/0503* (2013.01); *A61G 12/001* (2013.01); *A61J 1/16* (2013.01)

(58) Field of Classification Search
CPC ........ A47F 7/00; A47F 7/0028; A47F 7/0021; A47F 7/0035; A61G 7/0503; A61G 13/00; A61G 12/001; A61B 19/0256; A61B 19/0259; A61B 19/0271; A61B 2019/0258; A61B 2050/21; A61B 50/20; A61B 50/22; A61B 50/24; A61M 5/1418; A61M 5/0008; A61M 5/3278; B01L 9/06; B43M 99/008; A47C 21/00; F16L 3/223; B25H 3/003; B25H 3/00; B25H 3/04; B25H 3/06; A47B 81/005

USPC ......... 211/85.18, 85.13, 10, 86.01, 119.006, 211/70.6; 5/503.1, 507.1, 658; 206/446; 248/610, 612, 214, 215, 218.4, 229.15, 248/229.16, 229.26, 229.25, 227.3, 228.6, 248/230.7, 230.6, 228.7, 231.71, 231.81, 248/304, 339, 340; 422/300, 397, 310
See application file for complete search history.

(56) References Cited

U.S. PATENT DOCUMENTS

| 2,189,989 | A | * | 2/1940 | Lichtman | 211/74 |
| D173,818 | S | * | 1/1955 | Rogers | D19/78 |
| 3,473,772 | A | * | 10/1969 | Nilson | A61G 7/0503 248/214 |
| D239,334 | S | * | 3/1976 | Lowenstein | D19/77 |
| 4,406,368 | A | * | 9/1983 | Hermes | 206/371 |
| 4,449,750 | A | * | 5/1984 | Pultman | A61G 5/10 108/44 |
| 4,659,099 | A | * | 4/1987 | Malone | A61G 5/10 108/44 |
| 4,765,584 | A | * | 8/1988 | Lazaris | B25H 3/04 211/70.1 |
| 4,831,673 | A | * | 5/1989 | Winckler | 5/503.1 |
| 4,836,403 | A | * | 6/1989 | Blackmon | A47B 13/16 211/75 |
| 4,938,369 | A | * | 7/1990 | Carilli | 211/74 |
| 4,971,271 | A | * | 11/1990 | Sularz | 248/68.1 |
| 4,998,700 | A | * | 3/1991 | McKaig | A47C 21/00 248/214 |
| 5,148,919 | A | * | 9/1992 | Rubin | 206/443 |
| 5,263,578 | A | * | 11/1993 | Narvey | 206/232 |

(Continued)

*Primary Examiner* — Jennifer E Novosad
(74) *Attorney, Agent, or Firm* — Finn Simmensen

(57) ABSTRACT

A mobile phlebotomy-tool-storing-rack securable to a bedrail instead of the standard method of storing needed items upon the bed keeps needed materials within a practitioners reach without risk of misplacement or contact with the patient. Secure storage and placement of the vacuum tubes immediately following blood collection reduces risk of temporary misplacement and unintentional breakage.

9 Claims, 1 Drawing Sheet

(56) References Cited

U.S. PATENT DOCUMENTS

| | | | | |
|---|---|---|---|---|
| 5,365,623 | A | * | 11/1994 | Springer .............. A47C 21/003 248/207 |
| 5,447,243 | A | * | 9/1995 | Graber ......................... 211/69.5 |
| 5,458,394 | A | * | 10/1995 | Nichols .................. A47B 23/02 297/153 |
| 5,589,137 | A | * | 12/1996 | Markin et al. ................ 422/562 |
| 5,850,917 | A | * | 12/1998 | Denton et al. ................ 206/366 |
| 5,992,912 | A | * | 11/1999 | Zimm ........................... 294/143 |
| 6,349,827 | B1 | * | 2/2002 | Feder ............................ 206/373 |
| 6,390,293 | B1 | * | 5/2002 | Page et al. .................... 206/225 |
| 6,571,966 | B1 | * | 6/2003 | Hsiao ........................... 211/70.6 |
| 6,719,254 | B1 | * | 4/2004 | Speiser ................... A47K 1/09 248/311.2 |
| 6,842,922 | B2 | * | 1/2005 | Smeed .................... A61G 1/04 108/49 |
| 7,757,867 | B2 | * | 7/2010 | Hsieh ........................... 211/70.6 |
| 7,987,983 | B1 | * | 8/2011 | Guitreau ....................... 206/443 |
| 2003/0196922 | A1 | * | 10/2003 | Reaux .......................... 206/370 |
| 2007/0205170 | A1 | * | 9/2007 | Gainer et al. .......... 211/119.005 |
| 2010/0122962 | A1 | * | 5/2010 | Zhang et al. .............. 211/85.29 |
| 2011/0016632 | A1 | * | 1/2011 | Hopf ............................ 5/503.1 |
| 2013/0112636 | A1 | * | 5/2013 | Williams-Shelton et al. .......................... 211/85.13 |

\* cited by examiner

PHLEBOTOMIST'S UTILITY RACK WITH ATTACHMENT FEATURES

CROSS-REFERENCE TO RELATED APPLICATIONS n/a.

STATEMENT REGARDING FEDERALLY SPONSORED RESEARCH OR DEVELOPMENT n/a.

NAMES OF THE PARTIES TO A JOINT RESEARCH AGREEMENT n/a.

SEQUENCE LISTING n/a.

STATEMENT REGARDING PRIOR DISCLOSURES BY THE INVENTOR OR A JOINT INVENTOR n/a.

BACKGROUND OF THE INVENTION

Field of the Invention

The present invention relates generally to the field of phlebotomy, i.e., drawing a blood specimen.

The need for a product such as the "attachable drawing rack" has been evident for many years. In the field of phlebotomy, the procedure for drawing blood though simple is an important process and care must be taken to preserve the sample and reduce the need for a second draw.

This being said, the compartments used for storage of hypodermic needles, packets of gauze, sanitary wipes, vacuum tubes and other needed supplies have been lacking and disorganized. Many phlebotomist are forced to bring supplies to a patient's bedside. Problems with samples being lost or misplaced and chances of blood samples being damaged or tainted are always possible. This can cause loss of time and money and risk to patient health and hospital accountability.

As is discussed below, the present invention relates to a portable phlebotomy rack than can be securely attached to a bedrail by a clamp and then moved to a blood cart or tray.

BRIEF SUMMARY OF THE INVENTION

The phlebotomists utility rack with attachment features is made of a high density polyethylene (HDPE) material, and measures six and one-half inches in length by three and one-half inches in width by three inches in height.

On the left side of the top of rack are cylindrical indentations for the placement of vacuum tubes of specific sizes. In left-to-right order are indentations for two thirty five millimeter (35 mm), four thirteen millimeter (13 mm), three 11 millimeter (11 mm) and three seventeen (17 mm) placement indentations with a depth of two inches (2").

Next, as we look to the right, is a hollow slot measuring two and one-half inches by one half inch wide and one and a half inch deep where alcohol pads and other sanitizing wipes can be stored.

On the right of this hollow is another storage slot measuring two and a half inches by one and a half inch by two and a half inches in depth. This hollow is also for the storage of other materials used prior to the blood draw and after for wrappers, gauze and tape.

A semicircular channel projects from the left wall of the base.

The L-hooks one and a half inches in length extend downward on the rear of the unit for attachment purposes.

BRIEF DESCRIPTION OF THE DRAWINGS

For a further understanding of the objects and advantages of the present invention, reference should be had to the following detailed description, taken in conjunction with the accompanying drawing, in which like parts are given like reference numbers and wherein.

DETAILED DESCRIPTION OF THE PREFERRED EMBODIMENTS

Figure 1:
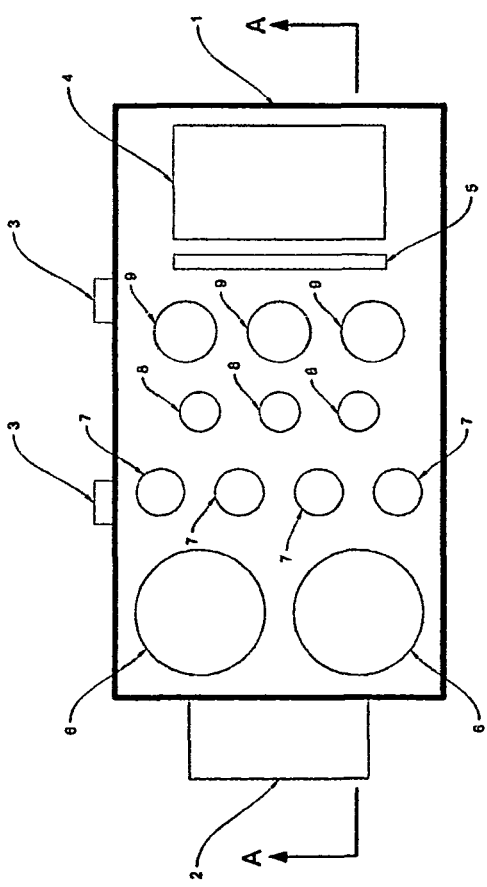
FIG. 1 is a top view of the phlebotomist's utility rack with attachment features in accordance with the present invention.

The invention will now be described with reference to FIG. 1, which shows a top view of a preferred embodiment of the phlebotomist's utility rack with attachment features ("phlebotomist's rack") in accordance with the present invention, having an outer wall 1, a semicircular clamp 2, two L-hooks 3, a temporary storage indentation 4 for used gauze, tape, pads and wrappers, a storage indentation 5 for alcohol wipes, two 35 mm holes 6 for vacuum tubes, four 13 mm holes 7 for vacuum tubes, three 11 mm holes 8 for vacuum tubes and used needles, and three 17 mm holes 9 for vacuum tubes.

Figure 2:
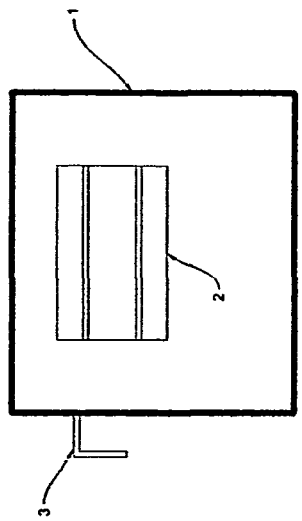
FIG. 2 is a side view thereof.

FIG. 2 shows a side view from the left of the phlebotomist's rack in accordance with the present invention, having the outer wall 1 of the rack, the semicircular clamp 2 and two L-hooks 3.

Figure 3:
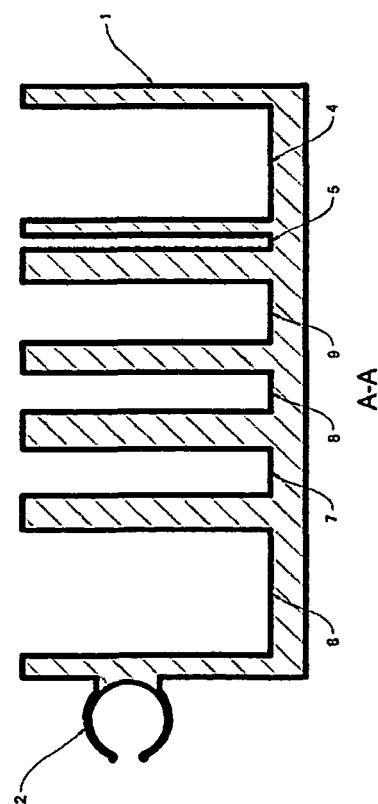
FIG. 3 is a front sectional view thereof.

FIG. 3 shows a sectional view of the phlebotomist's rack in accordance with the present invention, as seen from the front, showing the outer wall 1, the semicircular clamp 2, the temporary storage indentation 4, the storage indentation 5, the 35 mm holes 6, the 3 mm holes 7, the 11 mm holes 8, and the 17 mm holes 9.

The phlebotomist's utility rack with attachment features in accordance with the present invention can be made in variations that include a container for disposal of used hypodermic needles. Also in addition to the L-brackets, the rack can be created with a spring-loaded clamp. The hollows can be made in different diameters and spring-loaded clamps to accommodate different bed railings as well as the armrests of blood drawing chairs.

The phlebotomist's utility rack with attachment features in accordance with the present invention can be produced in various colors, and feature logos, emblems and or designs as a medical facility requests.

Features of the present invention include a portable phlebotomy rack made of high-density polyethylene (HDPE), measuring 6.5 inches by 3.5 Inches by 3 inches, having cylindrical indentations for storage of vacuum tubes of various specific sizes upon the top plane. Features also include a hollow slot for storage of sanitizing wipes in vertical placement upon the top plane and square-shaped indentations for storage of gauze, pads, tape and wrappers upon the top plane. Features also include a semi-circular clamp upon the left sidewall and two L-hooks upon the front sidewall.

The Attachable Drawing Rack makes bedside venipuncture safer, faster, more convenient and more hygienic to complete than ordinary methods. It can be easily and securely attached upon phlebotomy trays and upon the side-rails of a hospital bed. By storing the necessary tools and the disposable materials generated from use of such tools and ensures a clean and sanitary environment for the phlebotomist and the patient. It eliminates the risk of phlebotomy tools causing discomfort to the patient when they become misplaced in a patients bed, and also the accidental, temporary misplacement of tube-stored blood samples. Unlike products with similar intentions the rack is easy to use and requires very little manual dexterity and/or grip strength.

As can be seen from the drawing figures and from the description, each embodiment of the phlebotomist's utility rack with attachment features in accordance with the present invention solves a problem by addressing the need for clean, sanitary, convenient storage and disposal of items used by a phlebotomist and by being easy to use.

While the specification describes particular embodiments of the present invention, those of ordinary skill can devise variations of the present invention without departing from the inventive concept.

Although specific embodiments have been illustrated and described herein, those of ordinary skill in the art will appreciate that any arrangement calculated to achieve same purposes can be substituted for the specific embodiments shown. This disclosure is intended to cover any and all adaptations or variations of various embodiments of the invention. It is to be understood that the above description has been made in an illustrative fashion, and not a restrictive one. Combinations of the above embodiments, and other embodiments not specifically described herein will be apparent to those of skill in the art upon reviewing the above description. The scope of various embodiments of the invention includes any other applications in which the above structures and methods are used. Therefore, the scope of various embodiments of the invention should be determined with reference to the appended claims, along with the full range of equivalents to which such claims are entitled.

In the foregoing description, if various features are grouped together in a single embodiment for the purpose of streamlining the disclosure, this method of disclosure is not to be interpreted as reflecting an intention that the claimed embodiments of the invention require more features than are expressly recited in each claim. Rather, as the following claims reflect, inventive subject matter lies in less than all features of a single disclosed embodiment. Thus the following claims, and such other claims as may later be added, are hereby incorporated into the description of the embodiments of the invention, with each claim standing on its own as a separate preferred embodiment.

The invention claimed is:

1. A phlebotomist's rack, comprising:
an upward-facing top surface in which are formed a plurality of upward-opening indentations dimensioned for receiving vacuum blood tubes,
a plurality of said indentations being adapted to receive 35 mm vacuum tubes, a plurality of said indentations being adapted to receive 13 mm vacuum tubes, a plurality of said indentations being adapted to receive 11 mm vacuum tubes, and a plurality of said indentations being adapted to receive 17 mm vacuum tubes;
a first side surface;
at least one clamp projecting laterally from said side surface, said at least one clamp having vertically opposed upper and lower portions each extending horizontally and parallel to said side surface,
said upper and lower portions being spaced apart, said upper and lower portions and a portion of said first side surface between said upper and lower portions forming a cylindrical receiving space and being reversibly and oppositely vertically deformable to open said at least one clamp to adapt said at least one clamp to clamping said first side surface to a bed-rail,
said at least one clamp defining said receiving space to extend laterally along said side surface more than twice the diameter of said receiving space,
the rack having a second side surface, substantially perpendicular to said first side surface,
said second side surface having at least one horizontally-projecting, downward-pointed L-hook,
said at least one L-hook projecting horizontally approximately 0.5 inch from said second side surface and then downwardly approximately 1 and 3/16 inches,
said at least one clamp and said at least one L-hook cooperating to adapt the rack for stable mounting alternately on a bedrail and on a blood cart or tray.

2. A phlebotomist's rack, comprising:
an upward-facing top surface in which are formed a plurality of upward-opening indentations dimensioned for receiving vacuum blood tubes;
a first side; and
a second side,
at least one bed-rail-engageable clamp projecting laterally from said first side, said at least one clamp having vertically spaced-apart, mutually opposed upper and lower portions, said upper and lower portions and a portion of said first side between said upper and lower portions forming a cylindrical receiving space and being reversibly vertically deformable to open said at least one clamp to adapt said at least one clamp to clamping said first side to a bed-rail,
said at least one clamp defining said receiving space to extend laterally along said first side more than twice the diameter of said receiving space; and
at least one phlebotomy-cart-engageable L-hook projecting horizontally approximately 0.5 inch from said second side and then downwardly approximately 1 and 3/16 inches,
said at least one L-hook spanning at least 3 inches of said second side,
said at least one clamp and said at least one L-hook cooperating to adapt the rack for stable mounting alternately on a bedrail and on a blood cart or tray.

3. The phlebotomist's rack of claim 2, wherein said first side and said second side face in mutually perpendicular directions.

4. The phlebotomist's rack of claim 3, wherein said first side and said top surface face in mutually perpendicular directions.

5. The phlebotomist's rack of claim 2, wherein said first side and said top surface face in mutually perpendicular directions.

6. The phlebotomist's rack of claim 2, wherein a plurality of said indentations being adapted to receive 35 mm vacuum tubes, a plurality of said indentations being adapted to receive 13 mm vacuum tubes, a plurality of said indentations being adapted to receive 11 mm vacuum tubes, and a plurality of said indentations being adapted to receive 17 mm vacuum tubes.

7. The phlebotomist's rack of claim 6, wherein said first side and said second side face in mutually perpendicular directions.

8. The phlebotomist's rack of claim 6, wherein said first side and said top surface face in mutually perpendicular directions.

9. The phlebotomist's rack of claim 6, wherein said first side and said top surface face in mutually perpendicular directions.

\* \* \* \* \*